(12) United States Patent
Harish et al.

(10) Patent No.: US 11,017,531 B2
(45) Date of Patent: May 25, 2021

(54) SHELL-CONSTRAINED LOCALIZATION OF VASCULATURE

(71) Applicant: CathWorks Ltd, Kfar-Saba (IL)

(72) Inventors: Omri Harish, Zur Yigal (IL); Ofek Shilon, Kfar-Saba (IL); Guy Lavi, Moshav Mishmeret (IL)

(73) Assignee: CathWorks Ltd, Kfar Saba (IL)

( * ) Notice: Subject to any disclaimer, the term of this patent is extended or adjusted under 35 U.S.C. 154(b) by 90 days.

(21) Appl. No.: 16/489,289

(22) PCT Filed: Mar. 8, 2018

(86) PCT No.: PCT/US2018/021614
§ 371 (c)(1),
(2) Date: Aug. 27, 2019

(87) PCT Pub. No.: WO2018/165478
PCT Pub. Date: Sep. 13, 2018

(65) Prior Publication Data
US 2020/0118264 A1  Apr. 16, 2020

Related U.S. Application Data

(60) Provisional application No. 62/468,961, filed on Mar. 9, 2017.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/504* (2013.01); *A61B 6/5205* (2013.01);
(Continued)

(58) Field of Classification Search
CPC ... G06T 7/0012; G06T 11/003; G06T 17/005; G06T 2200/08; G06T 2207/10116;
(Continued)

(56) References Cited

U.S. PATENT DOCUMENTS 6,047,080 A   4/2000  Chen et al.
10,342,442 B2 *  7/2019  Hattangadi ........ A61B 5/02755
(Continued)

*Primary Examiner* — Amara Abdi
(74) *Attorney, Agent, or Firm* — K&L Gates LLP; Louis C. Cullman; Dennis A. Majewski

(57) ABSTRACT

Methods of and systems for reconstructing a vascular tree shape from vascular segments imaged in a single source 2-D projection image are described. A structuring shape comprising spatial positions of reference anatomical elements is defined, such as vascular segments in the definition of a 3-D surface model corresponding to a surface defined by an anatomical structure such as a body organ (e.g., heart). The 3-D surface model is used to create a 3-D model of anatomical elements (e.g., additional vascular segments of a cardiac vasculature) imaged in a source 2-D projection image, by back-projection to the 3-D surface model. The 3-D surface model is optionally aligned by first aligning the source 2-D projection image to the structuring shape. In some embodiments, the source 2-D projection image is registered to the 3-D surface model through the structuring shape by the source image's initial use in defining the structuring shape.

28 Claims, 8 Drawing Sheets

(51) Int. Cl.
*A61B 6/00* (2006.01)
*G06T 11/00* (2006.01)
*G06T 17/00* (2006.01)

(52) U.S. Cl.
CPC .......... *G06T 11/003* (2013.01); *G06T 17/005* (2013.01); *G06T 2200/08* (2013.01); *G06T 2207/10116* (2013.01); *G06T 2207/30048* (2013.01); *G06T 2207/30101* (2013.01); *G06T 2210/41* (2013.01)

(58) Field of Classification Search
CPC . G06T 2207/30048; G06T 2207/30101; G06T 2210/41; G06T 7/593; G06T 2207/10012; G06T 17/00; A61B 6/50; A61B 6/5205; A61B 6/032
See application file for complete search history.

(56) References Cited

U.S. PATENT DOCUMENTS

| | | | |
|---|---|---|---|
| 10,441,239 B2 * | 10/2019 | Abe | A61B 6/542 |
| 2004/0066958 A1 * | 4/2004 | Chen | A61B 6/466 |
| | | | 382/128 |
| 2008/0205722 A1 * | 8/2008 | Schaefer | G06T 7/11 |
| | | | 382/128 |
| 2015/0339847 A1 * | 11/2015 | Benishti | G16H 50/30 |
| | | | 382/131 |
| 2015/0342551 A1 * | 12/2015 | Lavi | A61B 6/504 |
| | | | 600/431 |
| 2017/0018116 A1 * | 1/2017 | Sun | G06T 7/12 |
| 2019/0005737 A1 * | 1/2019 | Auvray | G16H 15/00 |

* cited by examiner

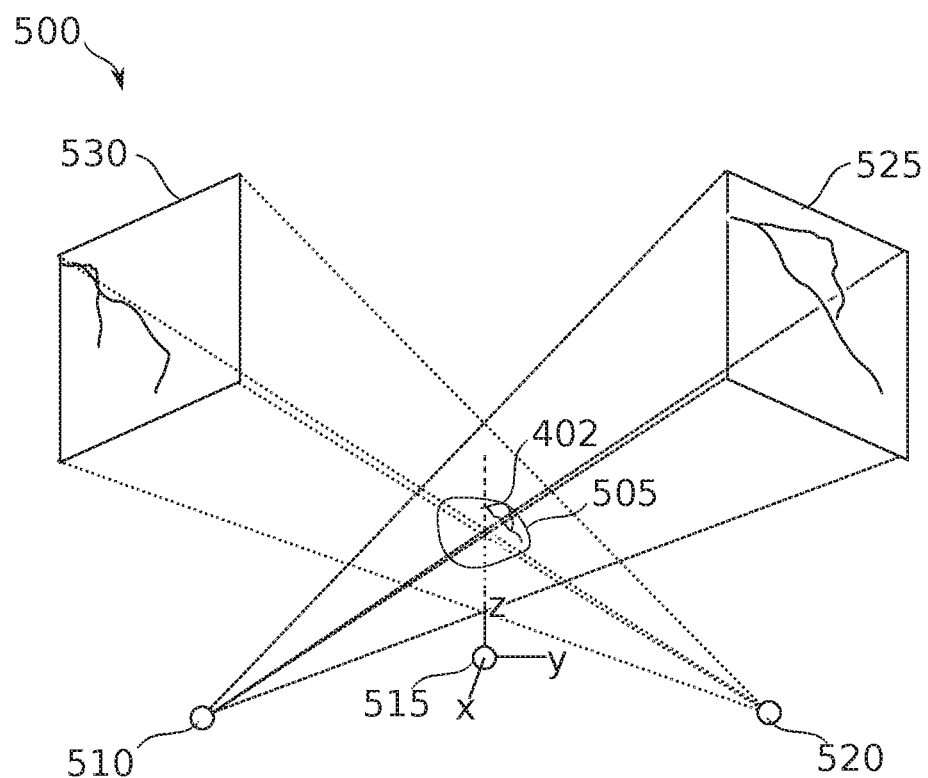
FIG. 5A
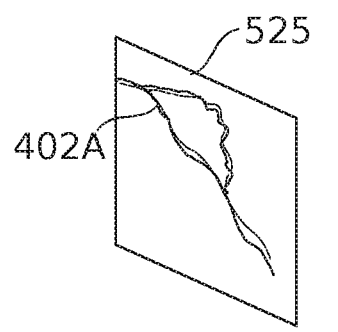 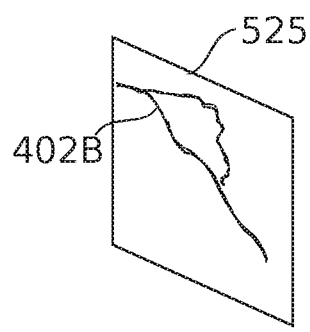 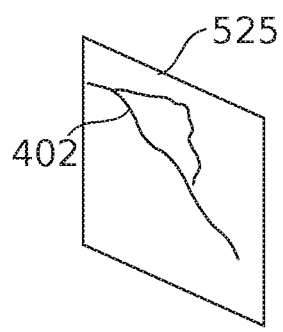
FIG. 5B     FIG. 5C     FIG. 5D

SHELL-CONSTRAINED LOCALIZATION OF VASCULATURE

PRIORITY CLAIM

This application is a national phase entry of PCT/US2018/021614, filed on Mar. 8, 2018, which claims priority to U.S. Provisional Patent Application No. 62/468,961, filed on Mar. 9, 2017, the entire disclosures of which are incorporated by reference herein.

TECHNICAL FIELD

The present disclosure, in some embodiments thereof, relates to the field of internal anatomical imaging, and more particularly, in some embodiments, to systems and methods for reconstruction of 3-D information from 2-D images of internal anatomy.

BACKGROUND

Methods of vascular modeling have been described in which a plurality of two-dimensional (2-D) angiographic images of a portion of a vasculature of a subject are received and processed to detect 2-D features, for example, paths along vascular extents. The features are projected into a three-dimensional (3-D) coordinate system to determine homologous features among vascular extents of blood vessels. In some embodiments, projection and/or image registration is iteratively altered to improve feature position matching. Based on 3-D vascular extents and their registration to 2-D images, additional features such as vascular width are optionally determined and added to the model.

Computer reconstruction of a 3-D coronary arterial tree may be performed from biplane angiograms acquired at arbitrary angles and without using calibration objects. Biplane projection images of the coronary structure are acquired, and from these, detecting, segmenting and identifying vessel centerlines and constructing a vessel hierarchy representation is performed. Bifurcation points and vessel diameters may be measured from in coronary angiograms. If biplane imaging geometry data is not available, biplane imaging parameters may be determined in terms of a rotation matrix and a unit translation vector based on the identified bifurcation points. Centerline correspondences of the two-dimensional arterial representations, may be calculated to recover the 3-D coronary arterial tree based on the calculated biplane imaging parameters, correspondences of vessel centerlines, and vessel diameters. The reconstructed 3-D coronary tree may be rendered. An optimal view of the vasculature may be determined from the reconstructed 3-D coronary tree to minimize vessel overlap and vessel foreshortening.

SUMMARY

There is provided, in accordance with some embodiments of the present disclosure, a method of reconstructing a vascular tree shape from vascular segments imaged in a source 2-D projection image. The example method comprises receiving a structuring shape comprising spatial positions of reference vascular segments, defining, based on the structuring shape, a surface model representing a surface along which the reference vascular segments extend, registering anchoring vascular segments shown in the source 2-D projection image to the structuring shape, and assigning 3-D positions to associated vascular segments shown in the source 2-D projection image, based on their occupation of the surface in common with the anchoring vascular segments.

In some embodiments, the surface model is spatially registered to the structuring shape.

In some embodiments, the method comprises defining the structuring shape using a plurality of 2-D projection images.

In some embodiments, the source 2-D projection image is one of the plurality of 2-D projection images, and the registering is performed as part of the defining.

In some embodiments, the defining uses convex curves defined by the extents of vascular segments visible in each of the plurality of 2-D projection images to define the surface model.

In some embodiments, the assigning uses back-projection of the imaged associated vascular segments in the source 2-D projection image to the surface model, based on the registering.

In some embodiments, the defining reduces errors in the back-projection using locations of at least partially-located shadow boundaries of a body organ at least partially defining the surface, imaged in the plurality of 2-D projection images.

In some embodiments, at least one of the associated vascular segments is back-projectable based on the registering to a plurality of alternative projection regions of the surface model; and the assigning includes selecting a selected projection region of the surface model for the at least one of the associated vascular segments.

In some embodiments, the selecting is based on the proximity of a portion of the at least one of the associated vascular segments to one or more of the anchoring vascular segments.

In some embodiments, the proximity is measured by distance in 3-D space.

In some embodiments, the proximity is measured by distance along surfaces of the surface model.

In some embodiments, the selecting is based on identification of regions where the image of at least one of the associated vascular segments changes in at least one of intensity and direction where it curves around an edge of the surface, as seen from the view point of the source 2-D projection image.

In some embodiments, the selecting is based on identification of regions where the images of at least two vascular segments in the source 2-D projection image intersect, and comprises assigning intersecting vascular segments to different projection regions of the surface model in the region of the intersection.

In some embodiments, the defining comprises registering a reference shape to fit a portion of the surface in a region defined by the structuring shape.

In some embodiments, the reference shape comprises a shape derived from anatomical atlas data, used as a geometrical approximation of the surface.

In some embodiments, the reference shape comprises a shape derived from 3-D imaging of a body organ imaged in the source 2-D projection image.

In some embodiments, the assigning comprises reducing errors in the back-projection, using as registration references locations of at least partially-determined shadow boundaries of a body organ at least partially defining the surface and imaged in the source 2-D projection image.

In some embodiments, the assigning comprises reducing errors in the back-projection, using as registration references locations of at least one vascular segment comprising changes in at least one of intensity and direction where the at least one vascular segment curves around an edge of the surface, as seen from the view point of the source 2-D projection image.

In some embodiments, the vascular segments are vascular segments of a coronary vasculature.

In some embodiments, the surface is a surface of a heart.

In some embodiments, the method comprises determining a length of at least one of the associated vascular segments, based on the distance for which the 3-D positions of the associated vascular segment extend along the surface model.

In some embodiments, the method comprises calculating vascular width along one of the associated vascular segments from the appearance of the associated vascular segment shown in the source 2-D projection image.

There is provided, in accordance with some embodiments of the present disclosure, a system of reconstructing a vascular tree shape from vascular segments imaged in a source 2-D projection image. The example system comprises computer circuitry configured to receive a structuring shape comprising spatial positions of reference vascular segments, define, based on the structuring shape, a surface model representing a surface along which the reference vascular segments extend, register anchoring vascular segments shown in the source 2-D projection image to the structuring shape, and assign 3-D positions to associated vascular segments shown in the source 2-D projection image, based on their occupation of the surface in common with the anchoring vascular segments.

In some embodiments, the computer circuitry is configured to spatially register the surface model to the structuring shape.

In some embodiments, the computer circuitry is configured to define the structuring shape using a plurality of 2-D projection images.

In some embodiments, the source 2-D projection image is one of the plurality of 2-D projection images, and the computer circuitry is configured to perform the registering as part of the defining.

In some embodiments, the computer circuitry is configured to assign using back-projection of the imaged associated vascular segments in the source 2-D projection image to the surface model, based on the registration of the vascular segments shown in the source 2-D projection image to the structuring shape.

In some embodiments, the computer circuitry is configured to calculate vascular width along one of the associated vascular segments using the appearance of the associated vascular segment shown in the source 2-D projection image.

Unless otherwise defined, technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment of the present disclosure, one or more tasks according to some exemplary embodiments of method and/or system as described herein are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein, a computer readable storage medium, which records data in a form of retrievable groups of digital bits, is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Additional features and advantages of the disclosed system, method, and apparatus are described in, and will be apparent from, the following Detailed Description and the Figures.

BRIEF DESCRIPTION OF THE FIGURES

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced. In the drawings:

FIGS. 5A-5D are diagrams that schematically illustrate generation of a structuring shape from plurality of 2-D projection images based on epipolar projection and motion compensation, according to some embodiments of the present disclosure;

DETAILED DESCRIPTION

Figure 1A:
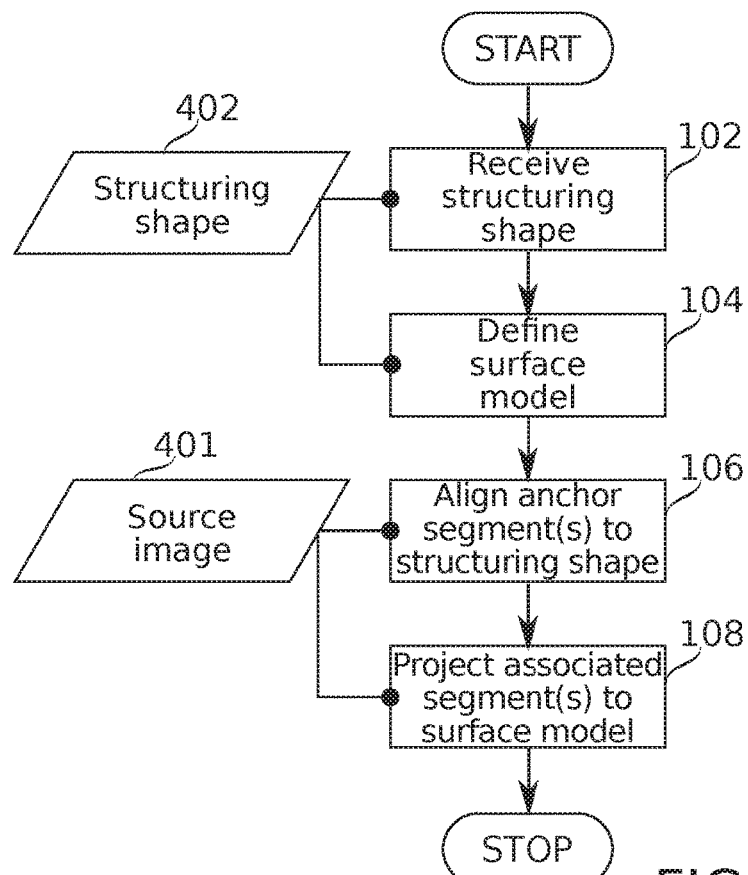
FIG. 1A is a flowchart schematically representing a method for using a single 2-D image to reconstruct 3-D positions of anatomical elements shown in the 2-D image, using anatomical conditions that restrict the anatomical elements to occupy positions near a geometrical 3-D surface defined by a surface model of an anatomically defined surface, according to some embodiments of the present disclosure.

The present disclosure, in some embodiments thereof, relates to the field of internal anatomical imaging, and more particularly, in some embodiments, to systems and methods for reconstruction of 3-D information from 2-D images of internal anatomy.

Overview

Single Image Reconstruction from Surface Constraints

An aspect of some embodiments of the present disclosure relates to a method of using a single 2-D image to reconstruct 3-D positions of anatomical elements shown in the 2-D image, using anatomical conditions that restrict the anatomical elements to occupy positions near a geometrical surface defined by a surface model of an anatomically defined surface. In some embodiments, the method is used to create 3-D reconstructions of 2-D angiographic projection images of a heart's vasculature, wherein the anatomical elements comprise vascular segments of the heart's vasculature, and the anatomically defined surface comprises a surface of the heart.

Arterial cardiac vasculature surrounds the volume of a heart with a branched, roughly basket-shaped structure. The volume of this structure appears flattened in projection 2-D images (e.g., 2-D images created using projection angiography techniques). In such a flattened view, depth information is suppressed, leading to potential distortions (e.g., where vessels are seen relatively "end on" instead of from the side) and branch-structure ambiguities (e.g., at crossing points).

In some embodiments of the present disclosure, certain quantitative calculations (e.g., of vascular segment and/or vascular tree flow resistance) are performed, based on 2-D image data. To achieve accurate results, suppressed depth information should be recovered, for example, to compensate for the effects of foreshortening on length measurements. In some embodiments, recovered depth information is used to identify regions where accurate calculation is potentially impaired due to a collapse of depth information. Optionally, determination of foreshortening is used as an indication that an image from a different angle should be used for calculations in some vascular tree portions. Moreover, it is of potential benefit to be able to display any given 2-D vascular image as a corresponding 3-D shape, to assist a user's (e.g., physician's, nurse's and/or technician's) visual grasp of the imaged scene. Exact recovery of the original 3-D shape is not necessarily required for all of these purposes.

It is noted that in a 2-D angiographic projection image, transparency of the imaged structure to the radiant energy type used potentially results in vascular segments appearing alongside one another, which are actually separated in depth. In some embodiments of the present disclosure, a geometrical surface defined by a surface model of an anatomically defined surface such as a heart is assumed to constrain positions which the anatomical elements of the heart vasculature can occupy. Herein, such a surface model is also referred to as a "shell", without restriction of generality. For example, once a heart shell is defined for a particular image (e.g., as a whole or partial surface of a hollow shape), there are, for a simplified case, only a few positions in depth (e.g., no more than two positions) that any vascular segment otherwise localized in the coordinates of the 2-D image plane can occupy. In the case of a balloon-like shell (non-infolded, and suppressing internal structure), there may be only two such surfaces: one extending along the closest half of the shell, and one extending along the further half of the shell. Moreover, transitioning between these two options is optionally limited to occur only at the edges of the shell, from the selected point of view.

Optionally, the surface model comprises a geometrical approximation of the actual anatomically defined surface. For example, the surface model is based on 3-D anatomical atlas data, and/or results from separately acquired 3-D images (CT images, for example) of the actual anatomically defined surface. Optionally, the geometrical approximation comprises a shape defined with few parameters. For example, defining parameters comprise parameters of a basic geometrical figure such as an ellipsoid, and/or node positions of a low polygon count mesh (e.g., 100 polygons or less).

In some embodiments, the surface model comprises a reference shape adjusted by a few parameters (e.g., scaling, rotation, and/or non-linear terms allowing anisotropic scaling) to fit observations indicating (but not necessarily providing in total) the shape of the actual anatomically defined surface. The reference shape comprises, for example, a parametrically defined surface, and/or a surface definition (such as a 3-D mesh) derived from direct 3-D imaging and/or from an atlas model of an anatomical structure which defines the anatomically defined surface.

Optionally, the observations used for the adjustments comprise fragmentary knowledge of the complete shape of the anatomically defined surface at the time of imaging. This fragmentary knowledge is extended to define a final surface model, optionally in combination with one or more other inputs. Optionally, the fragmentary knowledge comprises spatial positions of one or more reference vascular segments. These spatial positions are also referred to herein as a structuring shape. In some embodiments, a reference shape representing a standard heart is adjusted (e.g., by error-reduction fitting) to a size and position which best matches the calculated 3-D extents of the structuring shape.

In some embodiments, a structuring shape comprising 3-D extents of one, two or more blood vessel segments following the surface contour is calculated. Optionally, the calculating uses a plurality of angiographic images, for example as described in International Patent Publication No. WO2014/111930 to Kornowski, et al. The resulting structuring shape optionally approximates, without completely corresponding to, an actual 3-D shape of the vascular segments on which it is based—e.g., the structuring shape optionally allows an acceptable range of distortion in shape comprising a position difference of about 1%, 5%, 10%, or another larger, smaller or intermediate range of the total extent of the structuring shape. Furthermore, the actual 3-D shape of the vascular segments in each angiographic image used is optionally different among images, for example, due to imaging at a plurality of heartbeat and/or respiratory phases.

Optionally, other angiographic image information is used; for example, a shadow's edge (or portion thereof) defining an organ boundary, and/or features of vascular shape and/or intensity characteristic of vessels transitioning between front- and rear-facing surfaces of an organ. Optionally, non-angiographic image information is used. For example, heartbeat phase is tracked and used to select a reference shape which corresponds to an appropriate phase of the heartbeat as shown in the angiographic image from which a 3-D vascular shape is to be reconstructed. Optionally, a surface model reconstructed for one image is used as a basis for 3-D reconstruction of vasculature in another image; optionally, an image obtained from a different direction (e.g., the surface model is appropriately rotated for use in reconstruction) and/or at a different heartbeat phase (e.g., the surface model is appropriately scaled to account for cardiac muscle contraction/relaxation).

General Applications of Angiographic Reconstructions of Vascular Trees

3-D angiographic reconstructions produced using methods described herein may be used, in some embodiments, to support and/or guide diagnosis and/or treatment.

In some embodiments, a 3-D reconstruction of coronary vasculature centerlines is combined with vascular width along the centerline (for example, vascular width calculated from 2-D angiographic images) to create a vascular model from which vascular resistances may be calculated. In some embodiments, vascular widths are calculated using one or more of the same images which are used to produce the 3-D reconstruction of the coronary vascular centerlines. Vascular width may be measured from a 2-D image, for example, from the shape of one or more profiles of image values taken from along an axis perpendicular to a vascular centerline of an imaged vascular segment. Optionally, the cross-sectional area is calculated using the measured width as an overall diameter. Optionally, a plurality of diameters of a same position along the vascular centerline are measured in images taken from different angles (e.g., orthogonal angles), and the cross-sectional area is calculated using the plurality of diameters.

Measures of vascular resistance may be calculated using measurements of vascular width and/or vascular cross-sectional area. In some embodiments, vascular resistances of stenotic (e.g., narrowed by disease) regions are analyzed to generate an indicator of by how much blood flow is impaired through a current stenotic region, and/or how by much blood flow could be restored by a treatment to revascularized that region.

In some embodiments, this analysis comprises a comparison of stenotic regions with calculated non-stenotic ("revascularized") states of these same regions, for example to produce a calculated index of a potential for revascularization. In some embodiments, the index is comparable to a fractional flow reserve (FFR) measurement, e.g, where FFR indicates the ratio between blood pressure on two sides of a stenotic region, the calculated index may give a ratio between blood flow or another parameter of blood flow in a stenotic vs. a revascularized state.

Another use of a combined 3-D reconstructed vascular centerline and vascular width model is to determine the overall complexity of a subject's disease state, for example, using criteria established by a clinical score such as SYNTAX Score or another clinical scoring method.

In some embodiments, a 3-D reconstructed vascular centerline model (optionally with or without associated vascular width information) is used to visualize the shape of the heart vasculature, for example to help visualize the position of a catheter relative to the heart vasculature. This may be provided, optionally during a procedure underway, as a visual indication for a physician performing the procedure. A reconstruction technique which can potentially produce a 3-D reconstruction from an individual image has a particular potential advantage for producing a live 3-D view (e.g., a view which can be rotated to any suitable angle), even though the source image is a flat 2-D image taken from a single angle. Additionally or alternatively, it may be possible to produce 3-D reconstructions as needed during a procedure using fewer images.

Potential Technical Advantages of Single Image Reconstruction from Surface Constraints The above-described technique is used, in some embodiments, to address certain problems in the field of 3-D vascular reconstruction (that is, production of a 3-D model, for example of a vascular tree) which do not appear to have been fully overcome in the art. Techniques have been described to recover the 3-D information from a plurality of 2-D angiographic images—particularly images taken simultaneously from different viewing angles.

Due to noise-introducing factors such as heartbeat and respiratory movement, however, two angiographic projection images taken at an arbitrary interval from one another (e.g., not simultaneous and/or not phase-locked) are not necessarily images of the same heart geometry. International Patent Publication No. WO2014/111930 (to Kornowski, et al.) describes methods of using a plurality of such images to reconstruct in three dimensions a "consensus" shape for a vasculature, wherein the imaged vascular segments are typically the same (e.g., same vascular segments at different times), but identical geometrical shape is not necessarily assumed. Optionally, the reconstructed consensus shape is not the actual shape assumed by the vasculature in any of the individual images. Potentially, the reconstructed shape still approximates the actual shape closely enough for tasks such as branch identification, vasculature visualization, vascular tree-referenced measurements of vascular diameter, and the like (e.g., in support of one or more of the general applications of vascular reconstructions mentioned above).

However, there remain potential benefits from and/or uses for producing 3-D reconstructions from single images, based on the method outlined in the first section of this overview, and further detailed with respect to the figures herein:

- As distances between feature-matching alternatives get smaller (e.g., as may happen for the closer spacing of finer/higher branch order vascular segments), correspondences found within a consensus 3-D space are potentially more prone to matching error, particular as inter-image differences in the underlying 3-D geometry increase. By reconstructing from single images, this matching problem is reduced and/or circumvented.
- There can also be differences in which details are well-enough defined in each image to be extracted, complicating the problem of establishing cross-image correspondences. Single-image reconstruction potentially allows more efficient use of the vascular information available in each individual image.
- Single-image 3-D reconstructions are potentially faster; for example, insofar as iterative matching of features among a plurality of images can be reduced and/or avoided. Such speed enhancements can be of particular use for producing live 3-D displays; for example, during the actual angiography procedure.

Single-image reconstruction optionally reduces and/or circumvents a need to obtain (e.g., from two simultaneously imaged directions) and/or search for 2-D images which are sufficiently corresponding to give optimal results. Again, this potentially assists live-viewing of 2-D images as a corresponding stream of 3-D reconstructed representations.

Optionally, the results of single-image reconstruction are used to help identify similar 2-D images for use in pair-wise 3-D reconstruction, and/or to provide a basis for an initial transformation that can assist correspondence-based reconstruction. In some embodiments, features identified by 3-D reconstruction from a plurality of images are optionally used as input to single-image 3-D reconstruction—and results of the single-image 3-D reconstruction then used to inform a new round of 3-D reconstruction from a plurality of images, e.g., by assisting in the establishment of cross-image feature correspondences. This procedure is optionally iterated.

Optionally, single-image reconstruction assists identifying which parts of an image give the "best" (e.g., most nearly in-plane) view of vascular structures; e.g., by allowing a gradient of depth as a function of image plane position to be easily determined. For example, regions which extend through a smaller range of Z-depth in the reconstruction potentially are those which are less prone to foreshortening artifacts.

It is noted that the benefits and uses described do not absolutely require high-fidelity 3-D reconstruction. Rather, the 3-D reconstruction is optionally handled as a tool which need only be "good enough" for supporting other tasks such as those just described.

Terminology

In some embodiments, the single 2-D image comprises a projection image. Optionally, the single 2-D image comprises an angiographic image obtained by projection of radiant electromagnetic energy (e.g., X-rays) from a source, through a region of the imaged anatomical elements, and to a substantially planar detection region within which the projected radiant energy is detected by one or more sensors. Herein, except as otherwise noted, the term "angiography" refers particularly to imaging by such methods, and the term "angiogram" refers particularly to images taken by such methods.

In some embodiments, the anatomical elements comprise vasculature. Optionally, the vasculature is coronary vasculature; more particularly, in some embodiments, coronary artery vasculature. Additionally or alternatively, positions of another type of longitudinally extended anatomical element are imaged, comprising, for example, nerve and/or lymphatic tissue. The anatomical elements are optionally embedded within an organ defining the anatomically defined surface, surrounding it, and/or lining it internally.

In some embodiments, the anatomically defined surface with respect to which positions of the anatomical elements are bound is defined by a shape of a heart, chamber of a heart, and/or portion of a chamber of heart. Additionally or alternatively, the surface model comprises a geometrical surface modeling another anatomically defined surface, for example a surface defined by any suitable portion of a body organ, e.g., a brain, liver, lung, and/or intestine. Optionally, the anatomically defined surface is defined by a membrane associated with a body organ. Optionally, the surface model models an outer surface of the anatomically defined surface, and/or an inner surface. Optionally, the anatomically defined surface is defined within the interior of an anatomical structure, e.g., extending between an inner and outer surface of the organ, demarcating an internal structural boundary of the anatomical structure, etc.

Before explaining at least one embodiment of the present disclosure in detail, it is to be understood that features described are not necessarily limited in application to the details of construction and the arrangement of the components and/or methods set forth in the following description and/or illustrated in the drawings. Features are capable of other embodiments, or of being practiced or carried out in various ways.

Example of a 2-D Angiographic Projection Image

Figure 2:
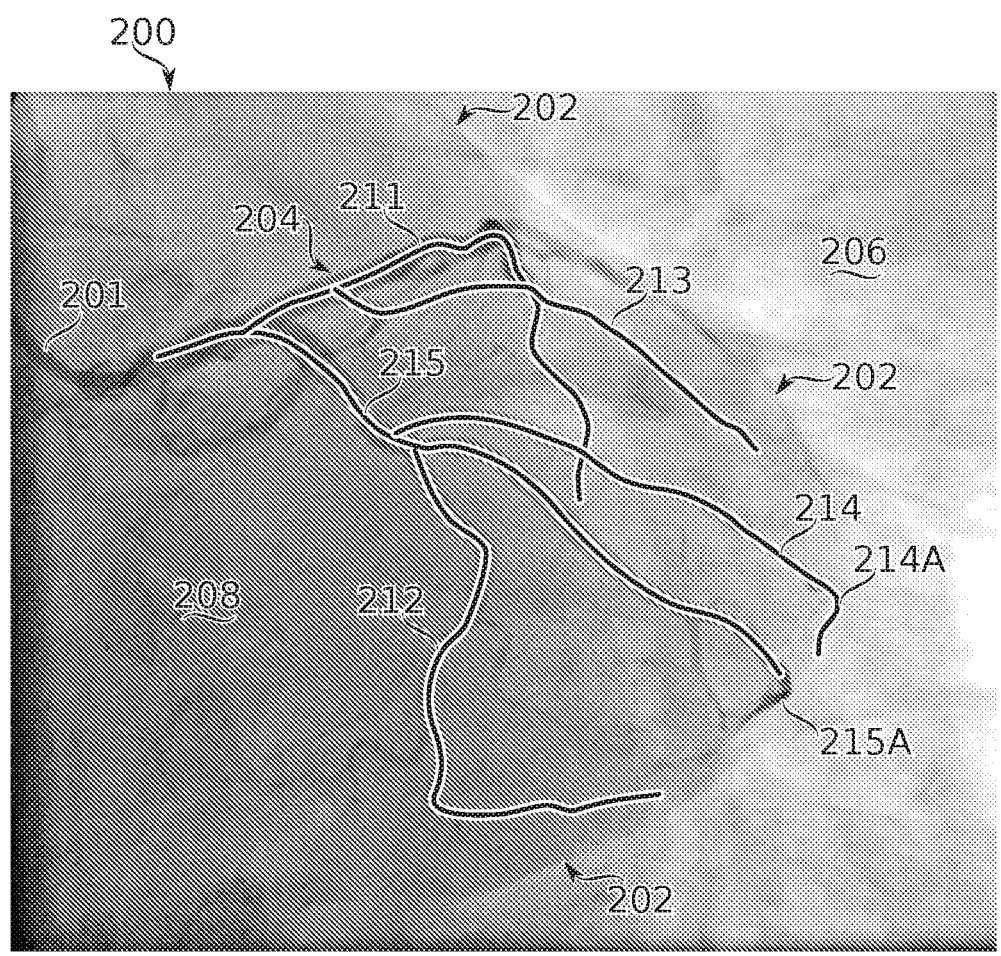
FIG. 2 is an angiographic image of a cardiac vasculature portion (left coronary artery), overlaid by partial tracings of major vascular branches, according to some embodiments of the present disclosure.

Before describing the method of FIG. 1A, reference is made to FIG. 2, which is an angiographic image 200 of a cardiac vasculature portion 204 (left coronary artery), overlaid by partial tracings of major vascular branches 211, 212, 213, 214, and 215, according to some embodiments of the present disclosure. FIG. 2 provides an orientation to certain features of 2-D angiographic projection images used in some embodiments of the current disclosure.

In the image, increased contrast of the vascular extents has been obtained by the injection of contrast agent from a site near the distal end of catheter 201. The contrast agent has been distributed into the left coronary artery and its branches, darkening the vasculature in the image. In angiographic image 200, vascular branches 211, 212, 213, 214, 215 appear flat. In the actual anatomy, however, these branches follow the three-dimensional curvature of the heart wall (external to the heart chambers). Thus, angiographic image 200 gives the appearance that vascular branches 211 and 213 cross near to each other, when in actuality they are separated in depth, extending along different portions of the heart wall (vascular branch 211 extends along the farther portion, and vascular branch 213 along the nearer portion). The apparent sharp bend of vascular branch 214 (at region 214A, coinciding with contour 202) is a result of depth foreshortening. Another indication of the suppressed appearance of depth is shown by the focal darkening at region 215A, where absorption is increased by the increased path length for absorption where vascular branch 215 has turned into the direction of depth.

In some embodiments, vascular branch 211 corresponds to the left anterior descending artery (LAD), including a portion of the left main coronary artery (LMCA); vascular branch 215 corresponds to the left circumflex artery (LCx); vascular branch 214 corresponds to a obtuse marginal (OM) branches of the left circumflex artery; vascular branch 212 corresponds to another branches of the left circumflex artery; and/or vascular branch 213 corresponds to a septal branch of the LAD.

Contour 202, in some embodiments, comprises a contour of a heart (indicated at regions along the contour) visible in angiographic image 200, and marking a boundary between a relatively lighter region 206, and a relatively shadowed region 208 wherein a heart and vasculature portion 204 thereof is imaged.

3-D Reconstruction Including Source Image Registration to a Structuring Shape

Reference is now made to FIG. 1A, which is a flowchart schematically representing a method for using a single 2-D image to reconstruct 3-D positions of anatomical elements shown in the 2-D image, using anatomical conditions that restrict the anatomical elements to occupy positions near a geometrical 3-D surface defined by a surface model of an anatomically defined surface, according to some embodiments of the present disclosure. The method is described in terms of vascular segments, however, it should be understood that the method also is applicable, changed as necessary, to other types of anatomical elements. Reference is also made to FIGS. 4A-4D, which schematically illustrates operations corresponding to blocks of FIG. 1A, according to some embodiments of the present disclosure. In some embodiments, the method of the flowchart is performed by a data processor configured to perform its operations, according to specified instructions.

Figure 4A:
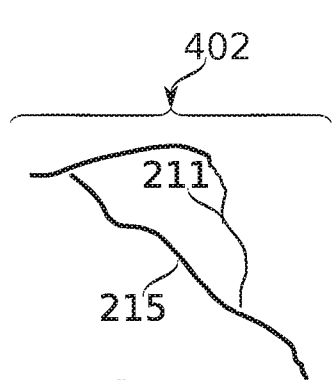
FIGS. 4A-4D are diagrams that schematically illustrate operations corresponding to blocks of FIG. 1A, according to some embodiments of the present disclosure.

At block 102, in some embodiments, the flowchart begins, and a structuring shape comprising spatial positions of reference vascular segments is received. The structuring shape optionally comprises a set of 3-D locations in space, e.g., linked along the paths of the reference vascular segments. FIG. 4A represents a structuring shape 402, comprising extents of vascular branches 211 and 215, which act as the reference vascular segments. A portion of vascular branch is drawn thin to indicate that this portion extends along the far side of the heart (e.g., is "deeper into the page" than vascular branch 215).

The structuring shape 402 is optionally generated from imaging data by any suitable means, for example as described in relation to FIGS. 5A-5D herein. A potential advantage of some embodiments of the present disclosure is that the structuring shape 402 can be relatively simple in structure (e.g., one or two vascular segments). This potentially reduces a burden on automatic methods of structuring shape generation for dealing with fine-scale anisotropies among images, movements large enough to create correspondence ambiguities, filling in of low contrast features (e.g., broken centerlines due to inconsistent contrast agent distribution), etc. Even if manual identification of the structuring shape is used, a simple one- or two-segment structuring shape is potentially relatively rapid to identify as an entry into fuller 3-D reconstruction of a vascular tree.

Features of the structuring shape 402, which make it suitable for use in the method of FIG. 1A, include that it comprises positions extending over enough of the anatomically defined surface (the outer heart surface, in this example), that the remainder of the anatomically defined surface can be determined to a required accuracy by some further means. In some embodiments, where fitting of a reference shape (derived, e.g., from an anatomical atlas and/or patient imaging) is used, the structuring shape preferably defines at least two mutually out-of-plane curvatures. This potentially reduces the chances for a degenerate result of the operations of block 104, wherein the degeneracy comprises a large range of fit parameters giving substantially equivalent quality of fit (minimization of distance error), even though only a smaller range of fit parameters is really useful as a basis for the 3-D reconstruction.

In FIGS. 4A-4D, the vascular features used as the basis of the structuring shape include the LAD 411, and the LCx 215. In most patients' anatomy, these vascular branches are long and mutually well-separated, so that they supply two well-defined, mutually out of plane curvatures. They are also large vessels, near to a commonly used contrast injection site, so that they are likely to be visible distinctly and completely in a large number of 2-D angiographic images.

It should be understood that other vascular branches are optionally selected as part of the structuring shape as appropriate; for example, using the right coronary artery (RCA) when a different part of the coronary vasculature is to be reconstructed, and/or using different branches according to individual differences in anatomy, lack of filling due to blockage, etc. Optionally, a structuring shape is generated based on non-vascular anatomical elements; for example, landmarks such as heart contour 202.

Figure 4B:
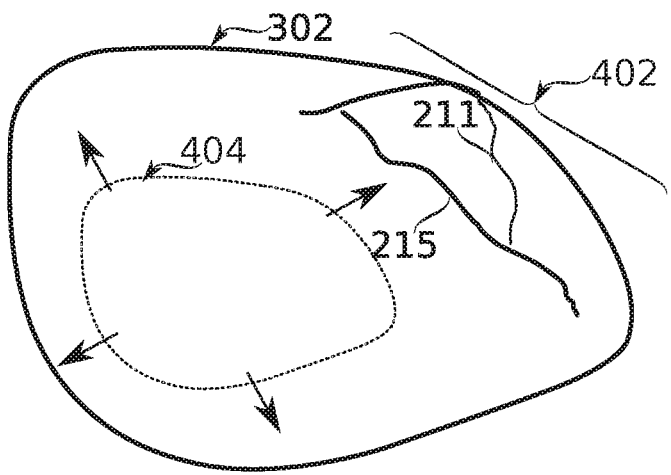

At block 104, in some embodiments, a surface model is defined in spatial registration with the structuring shape, representing an anatomically defined surface along which the reference vascular segments extend. Optionally, definition of the surface model is based on fitting of a reference shape to spatial constraints established by the structuring shape. In FIG. 4B, for example, a reference shape 404 (representing a portion of a heart) is illustrated at some arbitrary initial size. The attached arrows indicate transformation of reference shape 404 to the partial boundaries indicated by structuring shape 402 to obtain surface model 302, e.g., by any suitable fitting process of distance error minimization.

This reference shape 404 and/or surface model 302 is optionally defined from an atlas, from 3-D patient imaging data, and/or from other 2-D angiography images. As example of the latter of these is to use the 2-D angiography images to define a convex hull ("shell") corresponding to a surface of the heart using vascular centerlines viewed from different angles. A plurality of 2-D images comprising features (like coronary arteries) expected to extend along the surface of the heart are selected. The 3-D hull position (heart shell) is determined from the 2-D projections, for example by using the best-known projection parameters for each 2-D image plane, and recognizing that places where projection rays from different images intersect (or nearly intersect) are at or close to the heart shell. In between regions with features that can be localized by ray intersection, the hull can be defined using any technique known in the art, for example, polyhedra stitching, and/or fitting of a heart surface model.

It should be noted that for many purposes, accurate sizing and/or positioning of some parts of the surface model is more important than of other parts. For example, errors where there are no vascular segments of interest to reconstruction may not affect the final result. Errors where there are vascular segments of interest may be more critical, e.g., along contour 202 to which the vascular segment positions should be anchored (and not extending far beyond). In some embodiments, estimations of positions of contour 202 in the angiographic image are used as part of the information used to generate the surface model, for example, sizing and positioning a surface model template so that the boundaries of its surface coincide (in some plane and/or if projected in 2-D) with the position of contour 202. Because the contrast of contour 202 is potentially quite low, partial segmentations of contour 202 are optionally used. Optionally, regions of increased vascular contrast due to foreshortening where a vascular branch extends around contour 202 (such as the focal darkening at region 215A) are identified (e.g., by some variation of a threshold algorithm) and used in the generation of the surface model. For purposes of fitting, an attractive feature of using contour 202 and/or focal darkenings such as that at region 215A is that they have an inherent spatial relationship to the source 2-D projection image 401, which potentially assists in the registration operation of block 106.

Figure 4C:
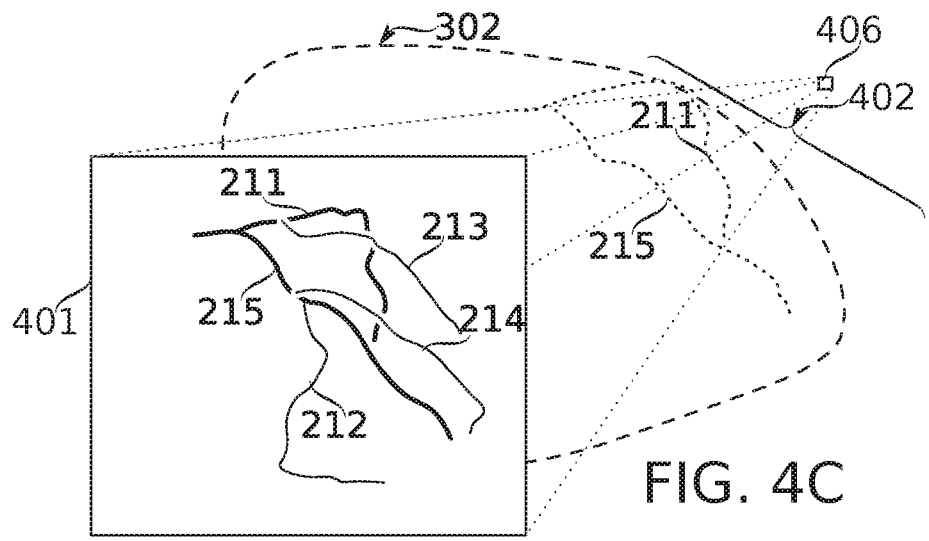

At block 106, in some embodiments, anchoring vascular segments shown in a source 2-D projection image 401 are registered to the structuring shape. Any suitable registration method which allows projecting the anchoring vascular segments of the source 2-D projection image 401 into coordinates occupying the space of the structuring shape, while ensuring alignment to the structuring shape, may be used. Providing an example of such a registration method, FIG. 4C shows an example of generic back-projection of an image 401 containing images of vascular branches 211, 215 (and other branches) into the space of structuring shape 402, based on knowledge of the relative position of radiative energy source 406, and the image plane of image 401.

Figure 1B:
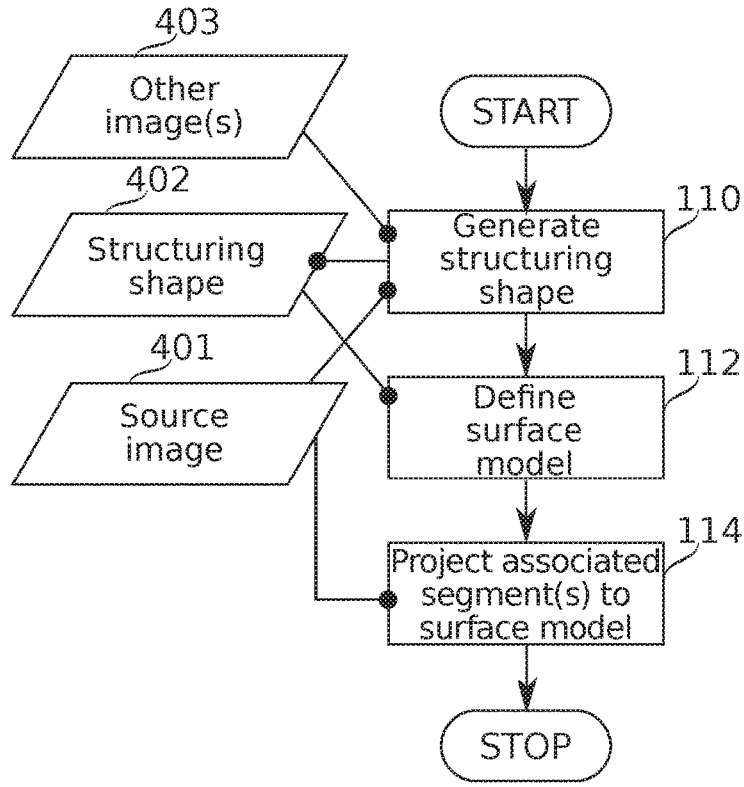
FIG. 1B is a flowchart schematically representing a variation of the method of FIG. 1A, wherein the structuring shape is initially defined in a way that includes the registering of block, according to some embodiments of the present disclosure.

As further detailed in relation to FIG. 1B and/or FIGS. 5A-5D, there may already be an available transformation through which the structuring shape is registered to anchoring vascular segments (e.g., vascular branches 211, 215) of the source 2-D projection image 401; for example, due to use of the source 2-D projection image 401 in generating the structuring shape. Optionally, for example if the structuring shape 402 was generated independently of the source 2-D projection image 401, a method such as that outlined in relation to Figure 5E is used, which may be viewed as a variant of the method of FIGS. 5A-5D that adds the source 2-D projection image 401 to a family of existing images which can be mapped to positions of the structuring shape. As already mentioned, in some embodiments, features such as contour 202 and/or the darkening at region 215A may have been related to one or more of the structuring shape and/or the surface model during the operations of block 102 and/or 104. This information can be used to assist registration of anchoring vascular segments to the structuring shape.

Figure 4D:
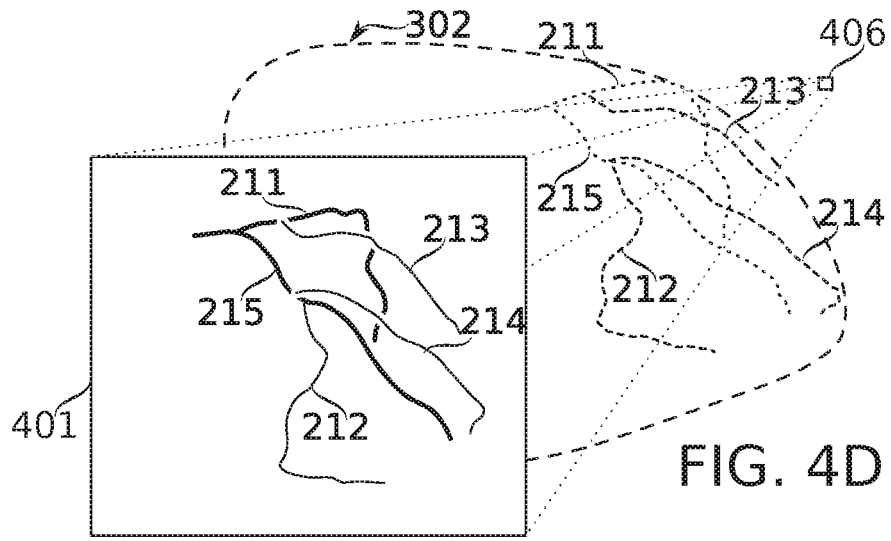

At block 108, in some embodiments, 3-D positions are assigned to associated vascular segments in the source 2-D projection image 401, and the flowchart ends. The assigning is based on the anatomical condition that the associated vascular segments and the anchoring vascular segments both occupy positions on or near the anatomically defined surface, as defined by the surface model. In some embodiments, the assigning uses back-projection of the imaged associated vascular segments in the source 2-D projection image 401 to the surface model, based on the registering performed at block 106. FIG. 4D shows, as examples, that segments 212, 213, and 214 have now been projected into to the 3-D space occupied by surface model 302, completing the reconstruction as a 3-D model of vascular extents.

In some embodiments, the resulting 3-D model of vascular extents is used as a basis for further structuring of vascular state data and/or as a basis for calculations relating to vascular function. For example, measurements of vascular width (optionally vascular radius, diameter, and/or estimated cross section; and optionally also measured from 2-D projection image 401) are, in some embodiments, associated to particular locations in the 3-D model along its vascular extents. In some embodiments, vascular widths for at least some portions of the 3-D model of vascular extents are calculated from another image, for example, another 2-D projection image registered to the 3-D model (e.g., by back projection). Optionally, the other 2-D projection image is taken from another angle and/or at another time than 2-D projection image 401. Using an image taken from a different angle is a potential advantage for obtaining details of vascular width in regions that 2-D projection image 401 images with foreshortening that may obscure local details. Using an image taken at a different time may be useful, for example, to view and/or compare vascular states (and in particular, different states of vascular width) at two or more different times: for example pre-treatment and post-treatment times, and/or to follow a time-course of disease development.

Optionally, the vascular widths are calculated (e.g., at least partially simulated) for a revascularized state of the vasculature extents, for example by modifying measured widths in stenotic areas. In some embodiments, the modifying comprises interpolating vascular widths between two non-stenotic regions. Optionally, an estimate of vascular function state is produced using the measured and/or calculated widths. In some embodiments, the estimating comprises comparison of stenotic regions with calculated and/or imaged non-stenotic ("revascularized") states of these same regions, for example to produce a calculated index of a potential for revascularization, and/or of a success level of revascularization achieved by a treatment. In some embodiments, the index is comparable to a fractional flow reserve (FFR) measurement, e.g, where FFR indicates the ratio between blood pressure on two sides of a stenotic region, the calculated index may give a ratio between blood flow or another parameter of blood flow in a stenotic vs. a revascularized state.

In some embodiments, there is a further problem addressed as part of the operations of block 108, which is to assign to each vascular branch (and/or portion thereof) a particular portion of the shell defined by surface model 302. For example, in the case of FIG. 4D, there are two possible shell portions that each segment can be assigned to: one closer to, and one further from the plane of image 401.

Any one or more of several pieces of information can be used as part of portion assignment. For example, for vascular segments that have more than one back-projection on the model, the back-projection is optionally chosen that has an origin closest (e.g., in direct 3-D distance, or distance over the shell surface) to the vascular segment from which it branches.

In some embodiments, the assignment uses the knowledge or assumption that some particular feature is on some particular shell portion. For example, it may be known from the spatial arrangement of the imaging setup that the root of the coronary artery (identified, for example, as the largest-diameter vascular portion, the position from which contrast agent was injected, etc.) is on some particular side of the surface model shell. Optionally, some other vascular portion is known to be on some particular side of the surface model shell. Then, in some embodiments, other feature positions are described in relation to this anchoring region of the vasculature. For example, the root of each branch is assigned to the same shell portion as the anchoring region.

Optionally, back-projection assignment is inverted for branch roots, and/or for extensions of each branch, whenever a shell-half crossing is detected. Optionally, features that indicate shell-half crossing include one or more of (and for example): a contrast increase such as the darkening at region 215A, a relatively rapid change in direction (such as seen at region 214A), and/or an encounter by a vascular segment with contour 202. Optionally, crossing points are taken as indications of two segments being on separate shell portions, since arterial branches tend to each supply regions separate from one another.

3-D Reconstruction with Source Image Pre-registered to a Structuring Shape

Reference is now made to FIG. 1B, which is a flowchart schematically representing a variation of the method of FIG. 1A, wherein the structuring shape 402 is initially defined in a way that includes the registering of block 106, according to some embodiments of the present disclosure. Reference is also made to FIGS. 5A-5D, which schematically illustrate generation of a structuring shape from plurality of 2-D projection images based on epipolar projection and motion compensation, according to some embodiments of the present disclosure.

At block 110, in some embodiments, the flowchart begins, and a structuring shape 402 comprising spatial positions of reference vascular segments is generated based on plurality of 2-D projection images, wherein the plurality of 2-D projection images include a source 2-D projection image for which a 3-D reconstruction of images vascular segments is to be generated. Insofar as generation of the structuring shape uses the source 2-D projection image, a registration between the anchoring vascular segments of the source 2-D projection image and the structuring shape is already established as part of this operation. The method used to create the structuring shape may be any suitable method, for example as described in relation to block 102 of FIG. 1A.

In particular, elements of a method based on centerline correspondences discovered using epipolar projection and motion compensation, for example as described in International Patent Publication No. WO2014/111930 (to Kornowski, et al.) may be used (e.g., block 30 of FIG. 14, in that reference, and described herein, for example, in relation to FIGS. 5A-5D). The vascular segments used from the source 2-D projection image in generation of the structuring shape become the anchoring vascular segments referred to, for example, in blocks 106 and 108 of FIG. 1A. Optionally, the vascular segments used are restricted to a small number of main vascular segments, for example, vascular segments comprising portions of the LAD (left anterior descending artery 211), LCx (left circumflex artery 215), and/or RCA (right coronary artery) branches of a coronary vasculature.

Some embodiments incorporate elements of a method of International Patent Publication No. WO2014/111930, as illustrated herein in FIGS. 5A-5D. In these embodiments, a plurality of images 530, 525 (two are shown; more are optionally used) comprising vascular segments and/or other anatomical elements of the structuring shape 402 are back-projected into a common coordinate system 515 (surface model 505 is shown for reference, but not yet defined at this stage). Optionally, at least one of the images 530, 525 is a source 2-D projection image 401 to be 3-D reconstructed. Optionally, other image(s) 403 are also provided for use in defining the structuring shape. The back-projection parameters are based, for example, on recorded information describing relative positions of the imaging planes of images 530, 525 and radiant energy sources 510, 520. For various reasons (such as body movements between images and/or imprecision in back-projection parameters), rays back-projected from corresponding features may not unambiguously intersect in the common coordinate system 515 without further processing. Corresponding features themselves are optionally undetermined initially. In some embodiments, a consensus structuring shape 402 is created, for example by expanding features of each image outward from their projected positions in the common-coordinate system 515 until the spatially expanded sets of projected features in the different images overlap with one another. Features whose expansions overlap each other establish their correspondences thereby. The whole system of correspondences is optionally adjusted for consistency. For example, variable scaling of distance along a vascular segment extent may be applied so that positions along the segment in two different image projections are mapped to each other in a 1:1 fashion. The region of overlap in turn defines "consensus" centerlines. These centerlines may be, for example, centerlines along which each consensus centerline portion is positioned where the total of distances to its corresponding representations in each image projection is minimized. Optionally a further criterion is applied to keep the consensus centerline smooth; for example, a smoothness constraint that penalizes high spatial frequency ("sharp" or "fast") changes in orientation, compared to low spatial frequency ("smooth" or "slow") changes in orientation.

In FIGS. 5B-5D, there is shown a re-projection of consensus centerline definitions 402A, 402B, and finally 402 into one of the images 525, used as an example. After each re-projection, remaining distance error between the image and the re-projection is determined. An error minimizing function is used to iteratively re-determine better-fitting projection parameters of each image back into common coordinate system 515. This changes the consensus centerline (e.g., from 402A to 402B), which can be re-projected again. The whole procedure can be applied iteratively until a satisfactory minimization of error is obtained, and a final structuring shape 402 is produced. This procedure has the potential advantage of not requiring very close initial spatial correspondence among back-projected features from different images. This allows images having significant differences in the vascular tree shape that produced them (for example, having different heartbeat phases) to be used in a common reconstruction procedure.

After completion of block 110, every image that was successfully used in the procedure is now registered to the structuring shape. Accordingly, the structuring shape is then available to be provided (as in block 102 of FIG. 1A); and, if the source 2-D projection image was one of the images used in generating the structuring shape, the source 2-D projection image is also registered to the structuring shape (as provided for in block 106 of FIG. 1A).

At block 112, in some embodiments, a surface model is defined in spatial registration with the structuring shape, representing an anatomically defined surface along which the reference vascular segments extend. Block 112 of FIG. 1B is performed as described for block 104 of FIG. 1A.

At block 114, in some embodiments, 3-D positions are assigned to associated vascular segments in the source 2-D projection image, and the flowchart ends. Block 114 of FIG. 1B is performed as described for block 108 of FIG. 1A.

Registration of a Source Image to an Existing or Modified Structuring Shape

Figure 5E:
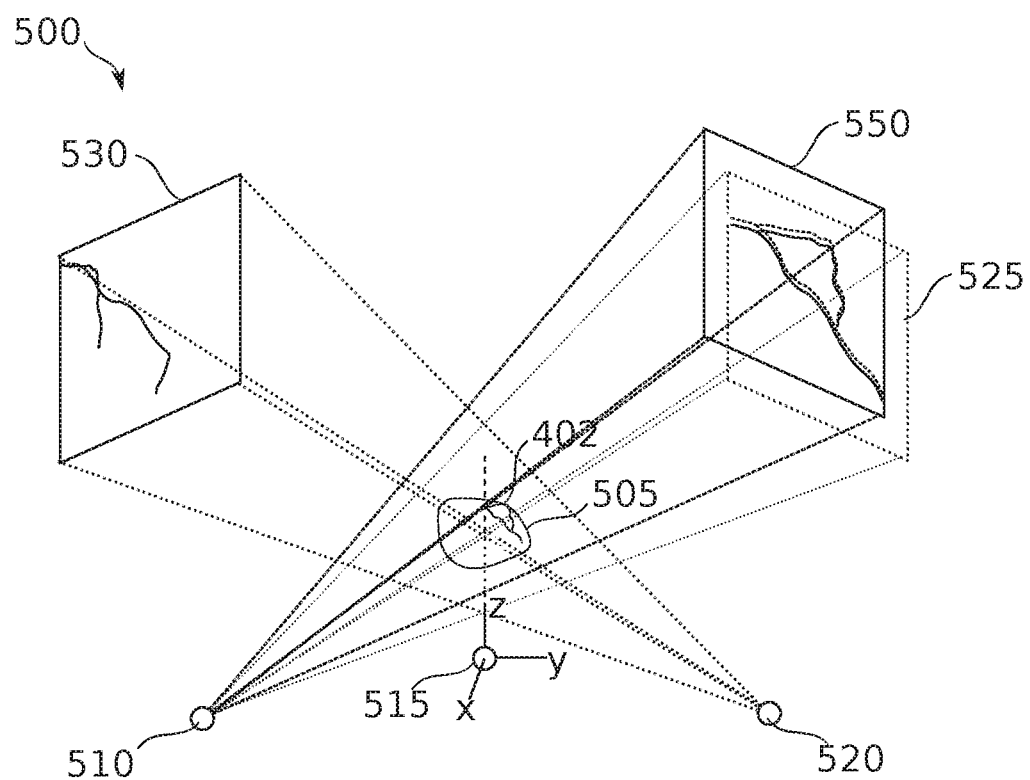
FIG. 5E are diagrams that schematically illustrates the registration of anchoring vascular segments and/or other anatomical elements of an additional image to a structuring shape generated, for example, by the procedure outlined with reference to FIGS. 5A-5D, according to some embodiments of the present disclosure.

Reference is now made to FIG. 5E, which schematically illustrates the registration of anchoring vascular segments and/or other anatomical elements of an additional image 550 to a structuring shape 402 generated, for example, by the procedure outlined with reference to FIGS. 5A-5D, according to some embodiments of the present disclosure. This, in some embodiments, is a method of carrying out the alignment of block 106. In some embodiments, the iterative procedure of FIGS. 5A-5D is simply restarted from where it left off, but with back-projected features of at least one new image (image 550) included. This may lead to the generation of a new structuring shape, insofar as adding the new image 550 alters the consensus centerlines (and, optionally, the definition of surface model 302). Optionally, the structuring shape is kept fixed, and iterative error-minimizing (or otherwise adjusted) redefinition of the transformation of image 550 into the common coordinate system 515 is used to make a match.

Registration Results

Figure 3A:
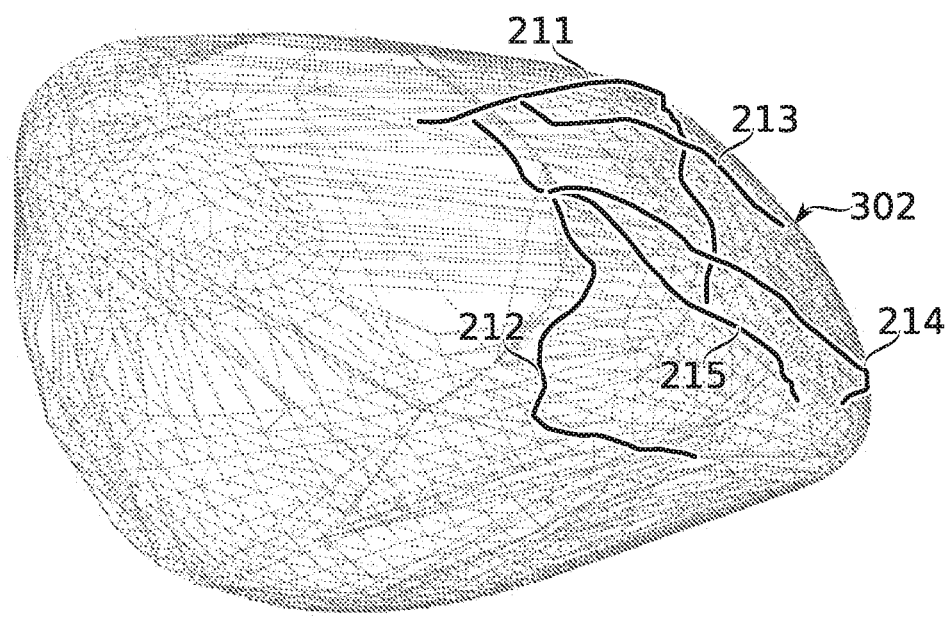
FIGS. 3A-3B show diagrams that illustrate results of mapping the angiographic branches of FIG. 2, to a 3-D shell representing geometry of a heart surface, according to some embodiments of the present disclosure.
Figure 3B:
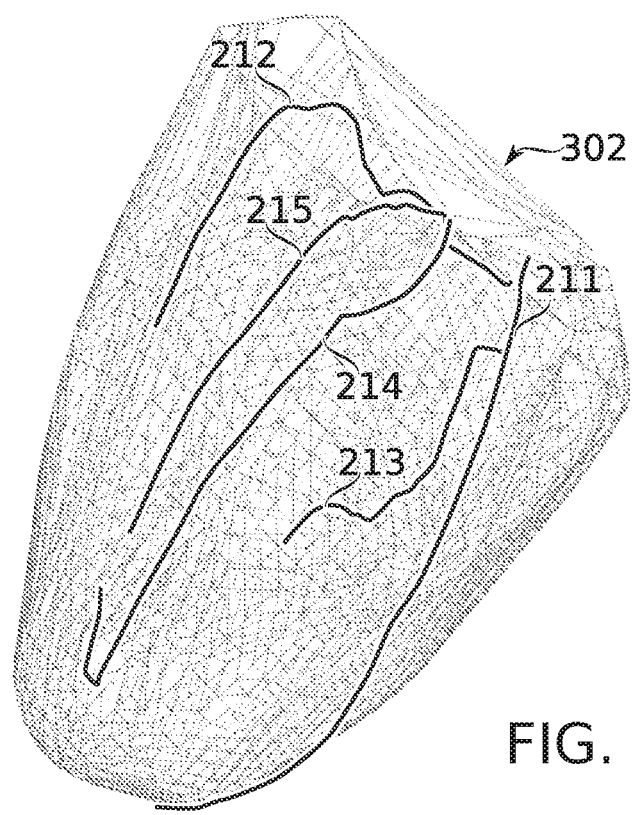

Reference is now made to FIGS. 3A-3B, which indicate results of mapping the angiographic branches 211, 212, 213, 214, 215 of FIG. 2, to a 3-D shell representing geometry of a heart surface, according to some embodiments of the present disclosure.

FIG. 3A shows the 3-D reconstructed vasculature from a viewpoint which is similar to the viewpoint of the imaging plane when the image of FIG. 2 was obtained. There is a slight rotation (e.g., around the long axis of surface model 302, but the general similarity of the reconstructed 3-D view and the 2-D image is apparent.

In FIG. 3B, surface model 302 has been more significantly rotated to present an entirely new vantage point on the reconstructed vasculature. The result illustrates how detailed vascular branch geometry in a single 2-D image can be converted to a 3-D representation of vascular centerlines, without a requirement for finding correspondences with similarly detailed features of a second 2-D image.

The result is available, for example: for display, for determination of which vascular segments are well-shown in the source 2-D projection image (e.g., show nearly from the side), and/or for estimation of vascular length information which is obscured by foreshortening in the original 2-D image.

Systems for Reconstruction from Single Images

Figure 6A:
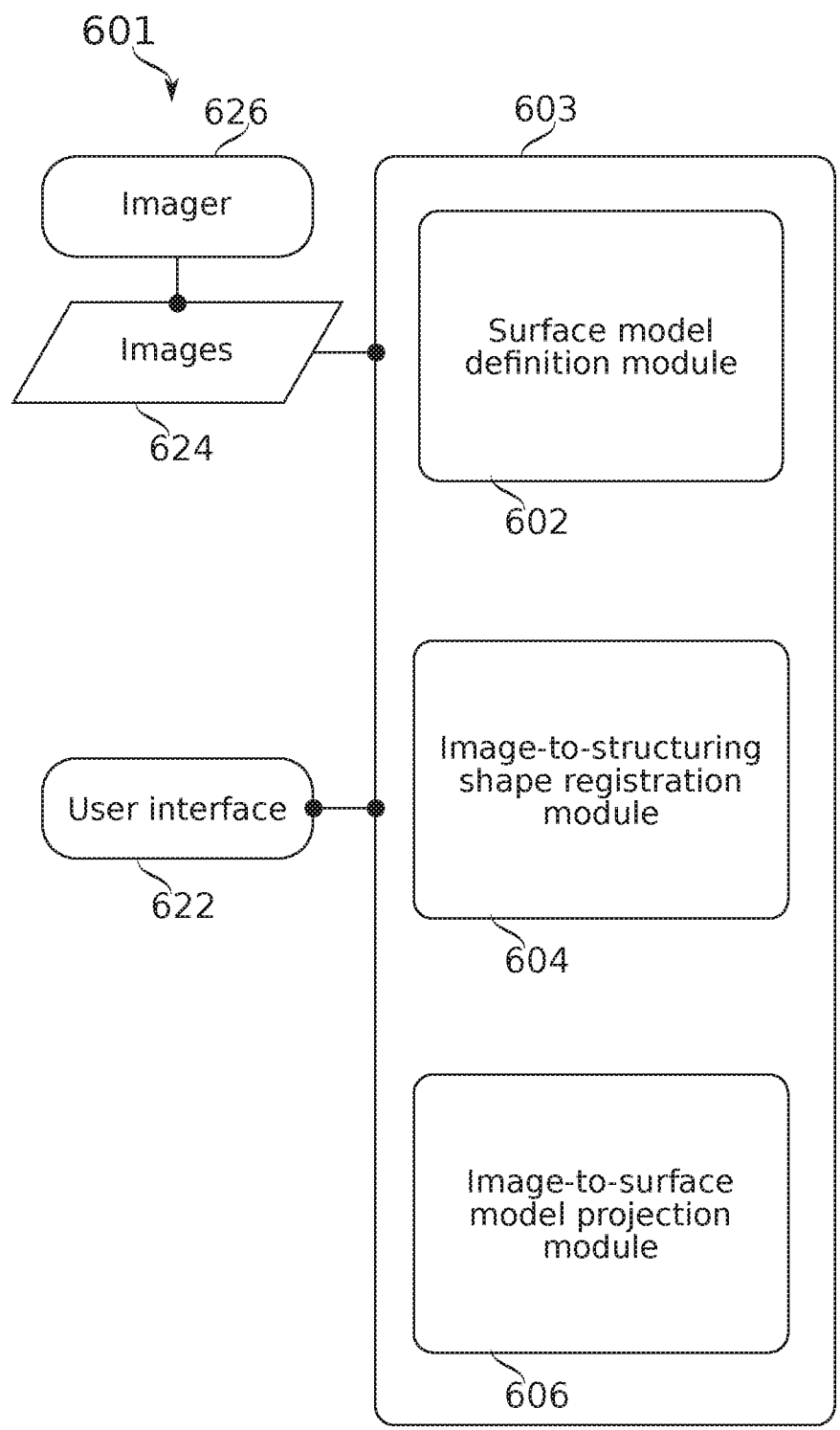
FIG. 6A is a diagram that schematically illustrates modules of a system for performing the reconstruction method of FIG. 1A, according to some embodiments of the present disclosure.

Reference is now made to FIG. 6A, which schematically illustrates modules of a system 601 for performing the reconstruction method of FIG. 1A, according to some embodiments of the present disclosure.

In some embodiments, system 601 comprises imager 616, which is configured to provide source 2-D projection images used, for example, by processor 603 to perform the method of FIG. 1A. In some embodiments, model results are displayed on user interface 612, for example, as display images indicating the 3-D structure of the reconstruction. User interface 612 optionally also is used to obtain user input, e.g., for selection of images 614 and/or interaction with display images. Processor 603, in some embodiments, is configured with modules (comprising, in some embodiments, software and/or dedicated processing hardware) performing the functions of modules 602, 604, and 606.

Module 602, in some embodiments, comprises a surface model definition module, configured by any suitable combination of hardware and software for carrying out operations as described in relation to block 104 of FIG. 1A.

Module 604, in some embodiments, comprises an image-to-structuring shape registration module, configured by any suitable combination of hardware and software for carrying out operations as described in relation to block 106 of FIG. 1A.

Module 606, in some embodiments, comprises an image-to-surface model projection module, configured by any suitable combination of hardware and software for carrying out operations as described in relation to block 108 of FIG. 1A.

Figure 6B:
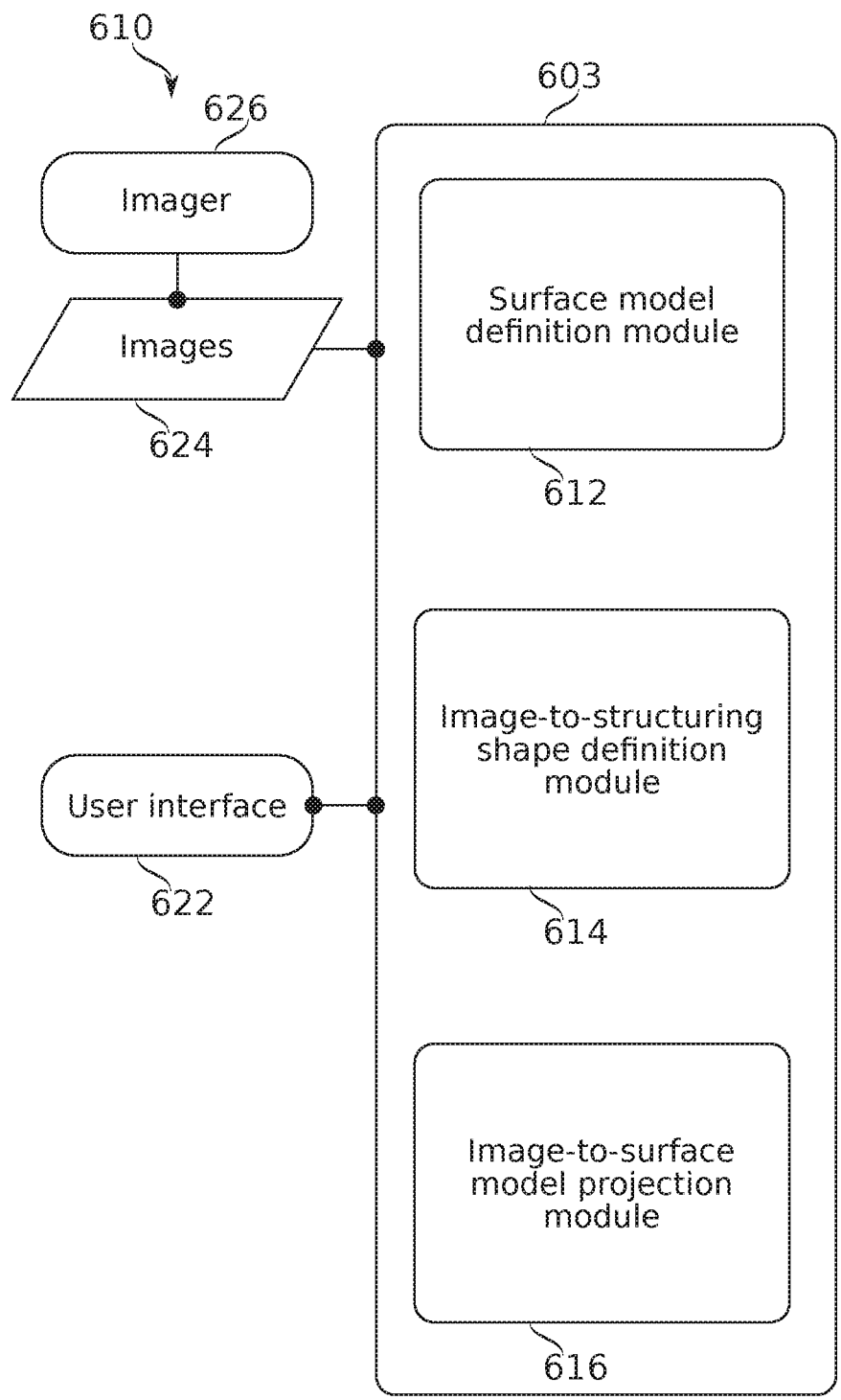
FIG. 6B is a diagram that schematically illustrates modules of a system for performing the reconstruction method of FIG. 1B, according to some embodiments of the present disclosure.

Reference is now made to FIG. 6B, which schematically illustrates modules of a system 610 for performing the reconstruction method of FIG. 1B, according to some embodiments of the present disclosure.

In some embodiments, system 610 comprises imager 616, which is configured to provide source 2-D projection images used, for example, by processor 603 to perform the method of FIG. 1B. In some embodiments, model results are displayed on user interface 612, for example, as display images indicating the 3-D structure of the reconstruction. User interface 612 optionally also is used to obtain user input, e.g., for selection of images 614 and/or interaction with display images. Processor 603, in some embodiments, is configured with modules (comprising, in some embodiments, software and/or dedicated processing hardware) performing the functions of modules 612, 614, and 616.

Module 612, in some embodiments, comprises a surface model definition module, configured by any suitable combination of hardware and software for carrying out operations as described in relation to block 112 of FIG. 1B.

Module 614, in some embodiments, comprises an image-to-structuring shape definition module, configured by any suitable combination of hardware and software for carrying out operations as described in relation to block 110 of FIG. 1B.

Module 616, in some embodiments, comprises an image-to-surface model projection module, configured by any suitable combination of hardware and software for carrying out operations as described in relation to block 114 of FIG. 1B.

In some embodiments, system 601, 610 is interconnected with one or more other systems (or modules of the same system) which further modifies and/or uses a vascular reconstruction produced by system 601, 610. For example, in some embodiments, one or more of the images 624 is also used to calculated vascular widths along vascular segment extents represented by the reconstruction. Insofar as the image 624 is already registered to the produced vascular reconstruction, the measured widths are readily associated to the reconstruction itself. In some embodiments, the reconstruction (optionally with associated vascular width data) is used as a basis for producing a display image, and/or for calculating vascular state data such as calculated indices of flow, and/or scores which indicate vascular lesion complexity.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this disclosure may be presented with reference to a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although features of the present disclosure have been described in conjunction with specific embodiments, it is evident that many alternatives, modifications and variations will be apparent to those skilled in the art. Accordingly, the descriptions herein are intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features, which are, for clarity, described herein in the context of separate embodiments, may also be provided in combination in a single embodiment. Conversely, various features, which are, for brevity, described in the context of a single embodiment, may also be provided separately or in any suitable subcombination or as suitable in any other described embodiment. Certain features described in the context of various embodiments are not to be considered essential features of those embodiments, unless the embodiment is inoperative without those elements.

The invention is claimed as follows:

1. A method of reconstructing a vascular tree shape from vascular segments imaged in a source 2-D projection image using anchoring segments and reference segments, the method comprising:

receiving, by computer circuitry, a structuring shape comprising 3-D spatial positions of reference vascular segments;

extending the spatial positions to define a computer-represented surface model representing an anatomical surface along which the reference vascular segments extend;

registering, by the computer circuitry, anchoring vascular segments shown in the source 2-D projection image to the spatial positions of the reference vascular segments on the surface model; and assigning, by the computer circuitry, 3-D positions to associated vascular segments shown in the source 2-D projection image, based on their occupation of the surface in common with the anchoring vascular segments.

2. The method of claim 1, wherein the surface model is spatially registered to the structuring shape.

3. The method of claim 1, further comprising defining the structuring shape using a plurality of 2-D projection images.

4. The method of claim 3, wherein the source 2-D projection image is one of the plurality of 2-D projection images, and the registering is performed as part of the defining.

5. The method of claim 3, wherein the defining uses convex curves defined by the extents of vascular segments visible in each of the plurality of 2-D projection images to define the surface model.

6. The method of claim 3, wherein the assigning uses back-projection of the imaged associated vascular segments in the source 2-D projection image to the surface model, based on the registering.

7. The method of claim 6, wherein the defining reduces errors in the back-projection using locations of at least partially-located shadow boundaries of a body organ at least partially defining the surface, imaged in the plurality of 2-D projection images.

8. The method of claim 6, wherein:
at least one of the associated vascular segments is back-projectable based on the registering to a plurality of alternative projection regions of the surface model; and
the assigning includes selecting a selected projection region of the surface model for the at least one of the associated vascular segments.

9. The method of claim 8, wherein the selecting is based on the proximity of a portion of the at least one of the associated vascular segments to one or more of the anchoring vascular segments.

10. The method of claim 9, wherein the proximity is measured by distance in 3-D space.

11. The method of claim 10, wherein the proximity is measured by distance along surfaces of the surface model.

12. The method of claim 8, wherein the selecting is based on identification of regions where the image of at least one of the associated vascular segments changes in at least one of intensity and direction where it curves around an edge of the surface, as seen from the view point of the source 2-D projection image.

13. The method of claim 8, wherein the selecting is based on identification of regions where the images of at least two vascular segments in the source 2-D projection image intersect, and comprises assigning intersecting vascular segments to different projection regions of the surface model in the region of the intersection.

14. The method of claim 1, wherein the defining comprises registering a reference shape to fit a portion of the surface in a region defined by the structuring shape.

15. The method of claim 14, wherein the reference shape comprises a shape derived from anatomical atlas data and is used as a geometrical approximation of the surface.

16. The method of claim 14, wherein the reference shape comprises a shape derived from 3-D imaging of a body organ imaged in the source 2-D projection image.

17. The method of claim 1, wherein the assigning comprises reducing errors in the back-projection, using as registration references locations of at least partially-determined shadow boundaries of a body organ at least partially defining the surface and imaged in the source 2-D projection image.

18. The method of claim 1, wherein the assigning comprises reducing errors in the back-projection, using as registration references locations of at least one vascular segment comprising changes in at least one of intensity and direction where the at least one vascular segment curves around an edge of the surface, as seen from the view point of the source 2-D projection image.

19. The method of claim 1, wherein the vascular segments are vascular segments of a coronary vasculature.

20. The method of claim 1, wherein the surface is a surface of a heart.

21. The method of claim 1, further comprising determining a length of at least one of the associated vascular segments based on the distance for which the 3-D positions of the associated vascular segment extend along the surface model.

22. The method of claim 1, further comprising calculating vascular width along one of the associated vascular segments from the appearance of the associated vascular segment shown in the source 2-D projection image.

23. A system of reconstructing a vascular tree shape from vascular segments imaged in a source 2-D projection image, the system comprising computer circuitry configured to:

receive a structuring shape comprising spatial positions of reference vascular segments;

define, based on the structuring shape, a surface model representing a surface along which the reference vascular segments extend;

register anchoring vascular segments shown in the source 2-D projection image to the structuring shape; and assign 3-D positions to associated vascular segments shown in the source 2-D projection image, based on their occupation of the surface in common with the anchoring vascular segments.

24. The system of claim 23, wherein the computer circuitry is configured to spatially register the surface model to the structuring shape.

25. The system of claim 23, wherein the computer circuitry is configured to define the structuring shape using a plurality of 2-D projection images.

26. The system of claim 25, wherein the source 2-D projection image is one of the plurality of 2-D projection images, and the computer circuitry is configured to perform the registering as part of the defining.

27. The system of claim 25, wherein the computer circuitry is configured to assign using back-projection of the imaged associated vascular segments in the source 2-D projection image to the surface model based on the registration of the vascular segments shown in the source 2-D projection image to the structuring shape.

28. The system of claim 23, wherein the computer circuitry is configured to calculate vascular width along one of the associated vascular segments using the appearance of the associated vascular segment shown in the source 2-D projection image.

* * * * *